(12) United States Patent
Westbrook et al.

(10) Patent No.: US 12,728,021 B2
(45) **Date of Patent: *Sep. 8, 2026**

(54) HANDLEBAR ADAPTER DEVICE

(71) Applicant: Form5 Prosthetics Inc., New Albany, OH (US)

(72) Inventors: Aaron Westbrook, New Albany, OH (US); Lindsey Austin, Lewis Center, OH (US); Jay Perkins, Pickerington, OH (US); Gavin Fancher, New Albany, OH (US)

(73) Assignee: FORM5 PROSTHETICS INC., Westerville, OH (US)

( * ) Notice: Subject to any disclaimer, the term of this patent is extended or adjusted under 35 U.S.C. 154(b) by 815 days.

This patent is subject to a terminal disclaimer.

(21) Appl. No.: 18/076,049

(22) Filed: Dec. 6, 2022

(65) Prior Publication Data

US 2024/0180722 A1 Jun. 6, 2024

(51) Int. Cl.

*A61F 2/58* (2006.01)
*A61F 2/80* (2006.01)
*B62K 21/12* (2006.01)

(52) U.S. Cl.

CPC ................ *A61F 2/588* (2013.01); *A61F 2/80* (2013.01); *B62K 21/125* (2013.01)

(58) Field of Classification Search

CPC .... A61F 2/54; A61F 2/58; A61F 2/582; A61F 2/585; A61F 2/586; A61F 2/588; A61F 2/78; A61F 2/80; A61F 2002/5096; A61F 2002/5098; A61F 2002/543; A61F 2002/546; A61F 2002/587; A61F 2002/785; A61F 4/00; G05G 1/54

See application file for complete search history.

(56) References Cited

U.S. PATENT DOCUMENTS

| | | | | |
|---|---|---|---|---|
| 2,333,009 | A | 10/1943 | Hosmer | |
| 2,905,492 | A | 9/1959 | Alexander | |
| 9,956,093 | B1 | 5/2018 | Harris | |
| 11,083,601 | B1 * | 8/2021 | Leonard | A61F 2/585 |
| 2005/0234564 | A1 | 10/2005 | Fink et al. | |
| 2015/0065310 | A1 * | 3/2015 | Quinn | A63B 21/0421 482/62 |
| 2023/0338172 | A1 | 10/2023 | Wellman et al. | |

FOREIGN PATENT DOCUMENTS

| | | | | |
|---|---|---|---|---|
| FR | 864055 | A * | 4/1941 | |
| GB | 108140 | A * | 7/1917 | A61F 2/588 |

(Continued)

OTHER PUBLICATIONS

Unyq, “Unyq raises $1 Million,” 3dprint.com, 2016.

(Continued)

*Primary Examiner* — Christie Bahena

(74) *Attorney, Agent, or Firm* — McNees Wallace & Nurick LLC

(57) ABSTRACT

A device for operating a vehicle involving handlebars using a residual arm. A user places a residual arm in a socket of the device, and the user may move the socket to translate force to a handlebar containment unit to cause movement of a handlebar. A handlebar channel of the handlebar containment unit receives and secures a portion of the handlebar.

9 Claims, 18 Drawing Sheets

(56) References Cited

FOREIGN PATENT DOCUMENTS

| | | | | |
|---|---|---|---|---|
| WO | 2016020317 A1 | | 2/2016 | |
| WO | WO-2021021754 A1 | * | 2/2021 | ............... B25B 5/06 |

OTHER PUBLICATIONS

Universal Design Style, "ProControl Cycling Hand Prosthesis," 2014.
Form5 Prosthetics, Youtube, 2023 5 Nonprofits to Watch,) The Columbus Foundation, 2023.
Strider + Ram Mounts, https://www.striderbikes.com/adaptive-strider-program; bears date of Oct. 21, 2022—downloaded Jun. 17, 2025.
Fillauer TRS, https://fillauer.com/bicycling-specific-devices/; undated—downloaded Jun. 17, 2025.
Limbo Foundation—Helpful Adaptations, https://limbbofoundation.co.uk/helpful-adaptations/; bears date of Feb. 19, 2024—downloaded Jul. 7, 2025.
Amber Henson, Riding a Bicycle When You Have an Upper Limb Difference, https://www.armdynamics.com/upper-limb-library/riding-a-bicycle-when-you-have-an-upper-limb-difference; bears date of Nov. 1, 2022—downloaded Jul. 7, 2025.
Koala Prosthetics, Say Hello to the ALX, https://www.yourkoalaa.com/sarahalx; undated—downloaded Jun. 17, 2025.
Strider, Adaptive Strider program—Custom Strider Bikes for toddlers, https://www.striderbikes.com/; undated—downloaded Jul. 7, 2025.

* cited by examiner

HANDLEBAR ADAPTER DEVICE

CROSS-REFERENCE TO RELATED APPLICATIONS

This application is filed as original and makes no priority claim.

TECHNICAL FIELD

The disclosed invention relates to a device that permits an individual missing a portion of at least one arm to operate a vehicle involving handlebars. An example embodiment includes a channel adapted to receive and secure a portion of a bicycle handlebar, and a receptacle adapted to receive a portion of a residual arm, and permit movement of the residual arm to define control of the bicycle.

BACKGROUND OF THE ART AND SUMMARY

Generally speaking, bicycles are operated through a combination of pedaling using one's feet, and steering the bicycle and balancing one's self using one's hands on two opposing handlebars of the bicycle. A number of other vehicles, including by way of example and not limitation, motorcycles, mopeds, ATVs, jet skis, snowmobiles, and the like also involve the use of handlebars for steering the vehicle and balancing one's self on the vehicle. Traditionally, operating handlebar vehicles has been difficult for arm amputees, individuals having congenital arm anomalies, and the like, because the ability to steer the vehicle and balance one's self while on the vehicle is limited when the individual lacks an ability to grasp by hand each of two handlebars. There is an unmet need in the prior art to provide a device that permits an individual missing a portion of at least one arm to operate a bicycle, and/or any other vehicle involving steering and balancing one's self using handlebars.

This and other unmet needs of the prior art are addressed by an adapter device as described in more detail below, as well as by a method of assembling said adapter device.

In one exemplary embodiment, a handlebar adapter device includes a main socket having a top edge, walls and a base, a stem, and a handlebar containment unit having a joint portion and a handlebar channel. The handlebar adapter device may be a prosthetic device configured to receive a residual arm. Specifically, the main socket may be configured to receive a residual arm, and move based on movement of the residual arm. The base of the main socket may be substantially perpendicular to the walls of the main socket. The base of the main socket may also be substantially flat. The stem may be configured to move based on movement of the main socket. The stem may be further configured to rotate about the joint portion of the handlebar containment unit. The handlebar channel of the handlebar containment unit may be configured to receive and secure a portion of a handlebar of any number of different handlebar vehicles, so that a user may move the main socket to directly cause movement of a handlebar.

In some exemplary embodiments, the main socket comprises plastic. The plastic may be 3D-printed plastic. Furthermore, in some embodiments, a portion of a perimeter of the top edge of the main socket is sloped below a remainder of the perimeter of the top edge. A top edge link may be configured to permit attachment of an additional apparatus to the main socket. A connection portion may be configured to link the main socket to the stem. The connection portion may further be configured to permit axial rotation of the main socket.

The handlebar containment unit may further comprise a ball and socket joint adapted to permit rotation of the stem and the main socket with respect to the handlebar containment unit. The handlebar channel may further comprise a circumference, and may be adapted to permit user variation of the size of the circumference. A length adjustment apparatus may permit adjustment of the length of certain exemplary embodiments. The length adjustment apparatus may comprise metal.

In one embodiment, a method for assembling a handlebar adapter device involves providing a main socket having a top edge, walls and a base, providing a stem, and providing a handlebar containment unit. The handlebar containment unit may comprise a joint portion and a handlebar channel. The aforementioned method may further involve configuring the main socket to receive a residual arm, and further configuring the main socket to move based on movement of the residual arm. The aforementioned method may also involve configuring the stem to move based on movement of the main socket, and further configuring the stem to rotate about the joint portion of the handlebar containment unit. The aforementioned method may additionally involve configuring the handlebar channel of the handlebar containment unit to receive and secure a portion of a handlebar.

Furthermore, the aforementioned method may involve configuring a portion of a perimeter of the top edge of the main socket to be sloped below a remainder of the perimeter of the top edge. A top edge link configured to permit attachment of an additional apparatus to the main socket may be provided. A ball and socket joint may be provided in the handlebar containment unit, and the ball and socket joint may be configured to permit rotation of the stem and the main socket with respect to the handlebar containment unit. A length adjustment device may also be provided in accordance with exemplary embodiments of the present invention.

Exemplary embodiments may be useful for permitting an individual missing a portion of at least one arm to control any number of different handlebar vehicles. A single exemplary device may be used, but in certain cases, more than one exemplary device may be used, such as when, by way of example and not limitation, an individual is missing portions of both arms.

BRIEF DESCRIPTION OF THE DRAWINGS

Novel features and advantages of the present invention, in addition to those expressly mentioned herein, will become apparent to those skilled in the art from a reading of the following detailed description in conjunction with the accompanying drawings. The present disclosure is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

DETAILED DESCRIPTION OF THE DRAWINGS

Various embodiments of the present invention will now be described in detail with reference to the accompanying drawings. In the following description, specific details such as detailed configurations and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Generally speaking, FIGS. 1 through 5 show one embodiment of an exemplary handlebar adapter device 10 adapted to receive and secure a portion of a bicycle handlebar, FIGS. 6 through 10 show another embodiment of an exemplary handlebar adapter device 44 adapted to receive and secure a portion of a bicycle handlebar, and FIGS. 11 through 22 show yet another embodiment of an exemplary handlebar adapter device 70 adapted to receive and secure a portion of a bicycle handlebar.

Figure 1:
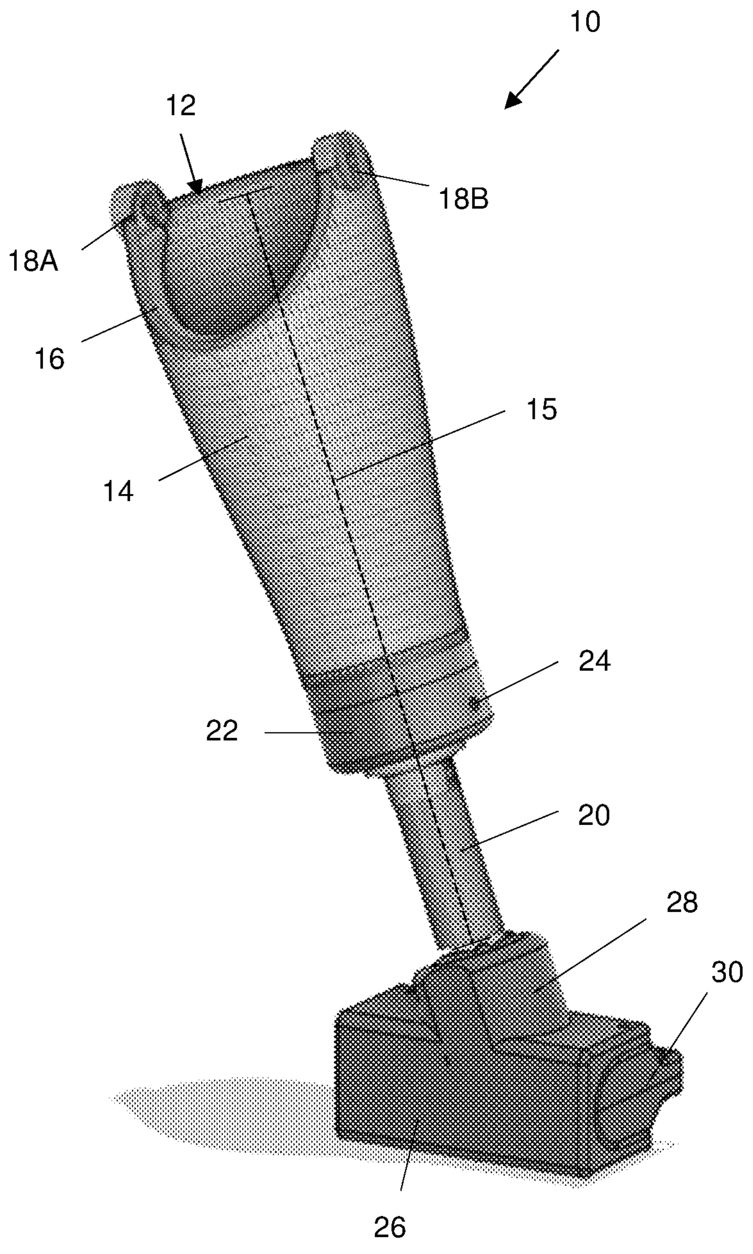
FIG. 1 is a perspective view of an exemplary handlebar adapter device adapted to receive and secure a portion of a bicycle handlebar.
Figure 2:
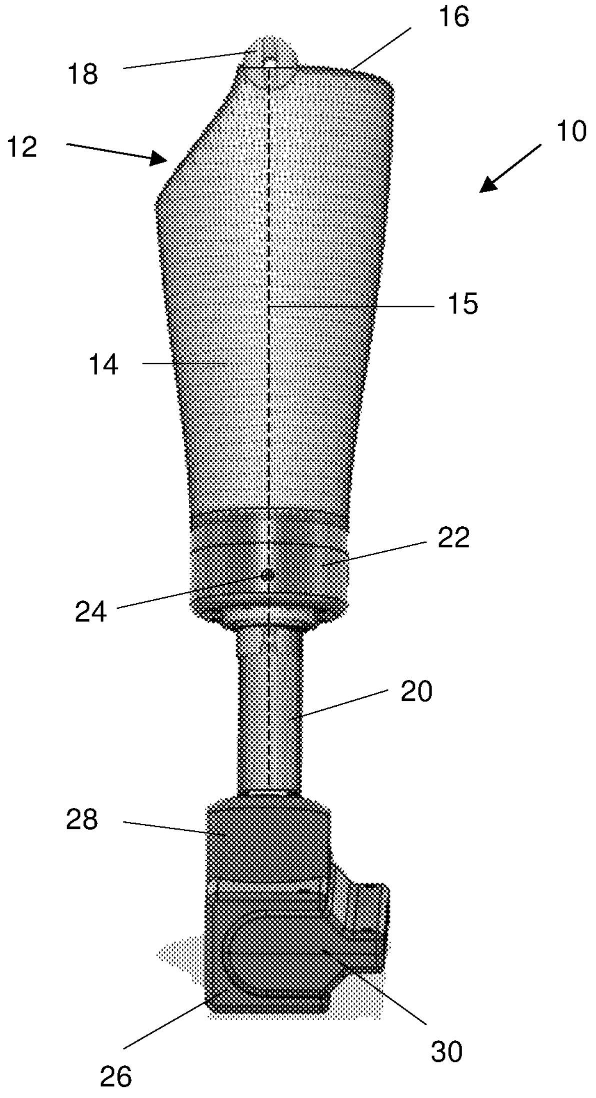
FIG. 2 is a side perspective view of the device of the FIG. 1 embodiment.
Figure 5:
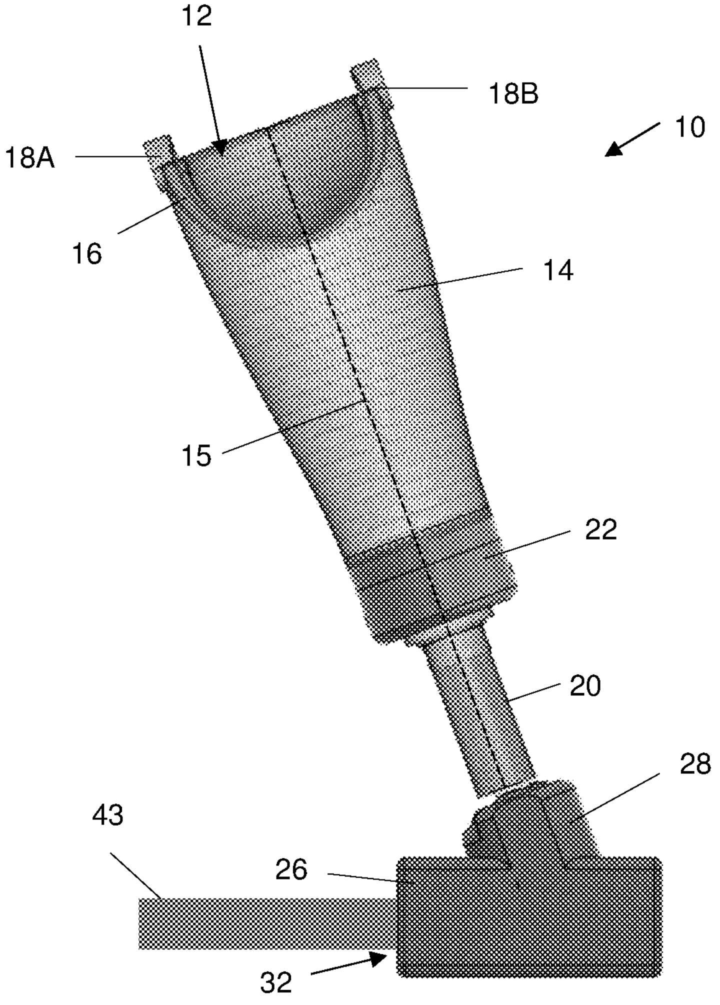
FIG. 5 is another perspective view of the device of the FIG. 1 embodiment.
Figure 6:
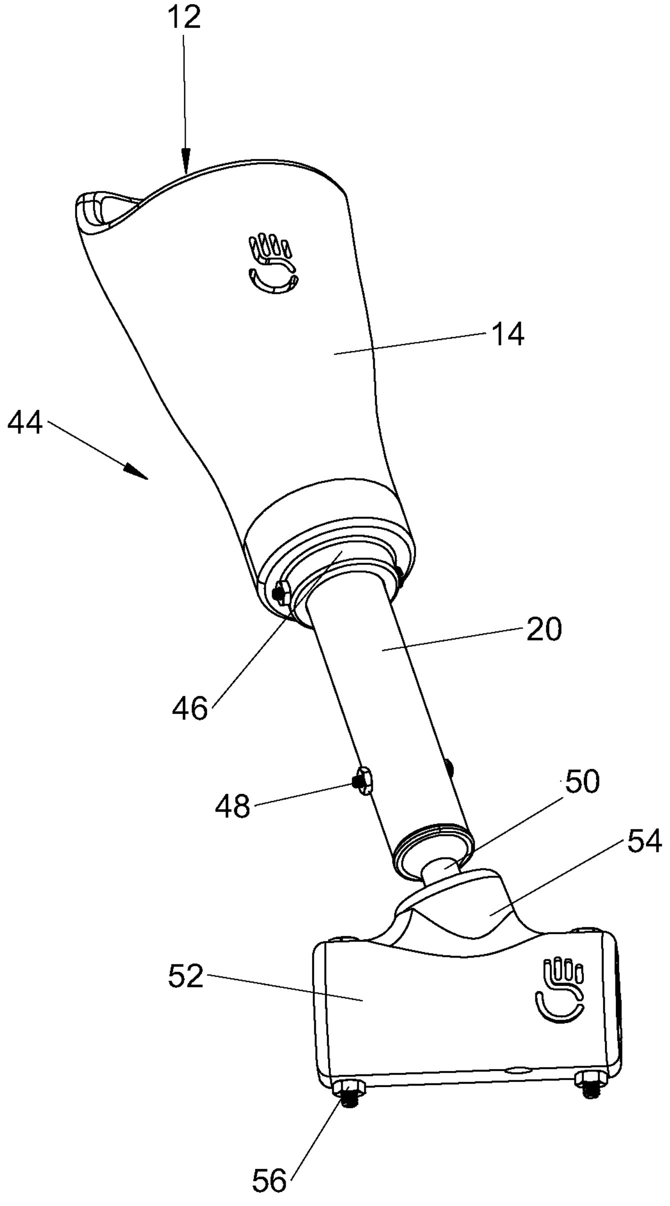
FIG. 6 is a perspective view of an alternative exemplary handlebar adapter device adapted to receive and secure a portion of a bicycle handlebar.
Figure 7:
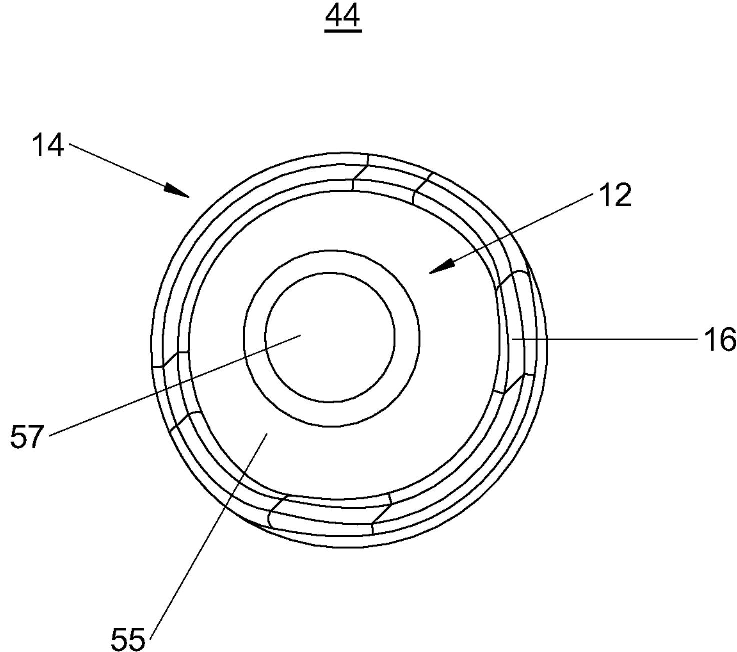
FIG. 7 is a top perspective view of a main socket of the FIG. 6 embodiment.
Figure 8:
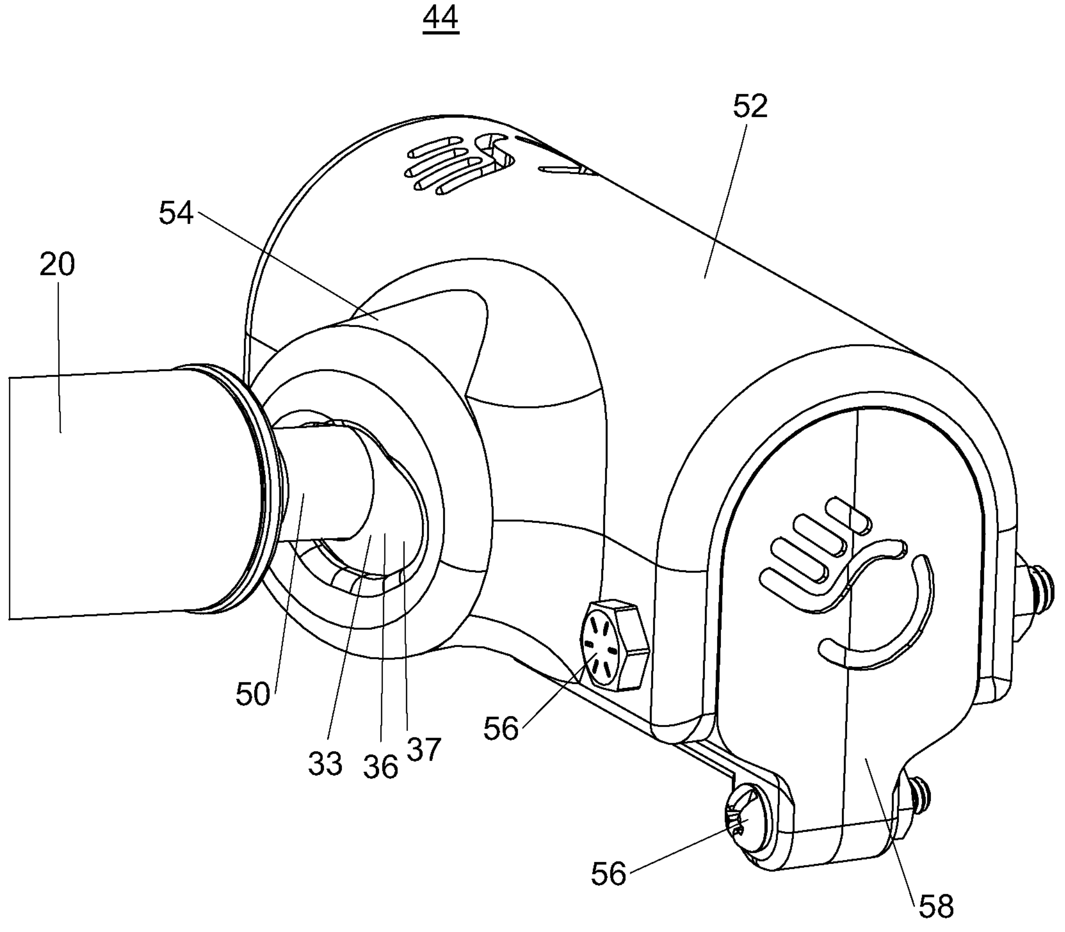
FIG. 8 is a perspective view of the handlebar containment unit of the FIG. 6 embodiment.

Referring initially to FIGS. 1-2 and 5, the device 10 may comprise a main socket 14 defining a perimeter of a receptacle 12 adapted to receive a portion of a residual arm (not shown). In certain preferred embodiments, the main socket comprises a substantially plastic socket. In certain preferred embodiments, the main socket may be adaptable to receive any number of different sized residual arms. By way of example and not limitation, the volume of the receptacle 12 may be modified in certain preferred embodiments. A residual arm is defined herein as a human arm lacking at least a portion of at least one typical arm bone. By way of example and not limitation, a residual arm may include an arm that has had a portion thereof amputated beyond the elbow, such that a user still has the elbow of the arm, but not the hand thereof. As another example not by way of limitation, a residual arm may include an arm that has been amputated before the elbow, such that the user still has at least a portion of the humerus of the arm, but not the elbow thereof. It will be apparent to one of ordinary skill in the art that exemplary device bodies may be assembled in any number of different shapes and/or sizes to accommodate any number of different arm amputees or individuals having congenital arm anomalies, regardless of residual arm shape.

Using the residual arm, the user may apply pressure to the walls or base of the receptacle 12 to direct force from the main socket 14 to a stem 20, which may act on a joint at a handlebar containment unit 26 to move the handlebar secured thereto in accordance with the user's desired steering and controls. By way of example and not limitation, the user may apply torque to the walls of the receptacle 12 to cause the stem 20 to rotate about the joint, which in turn may cause the handlebar containment unit to direct rotational force on the handlebar, which in turn may cause the bicycle to change direction in accordance with the user's desired steering. The user may also engage the walls or base of the receptacle 12 using one's residual arm to balance the bicycle and/or to balance the position of one's self on the bicycle.

The top edge 16 of the main socket 14 may surround an entry and exit region for positioning the residual arm in the receptacle 12 and for removing the residual arm from the receptacle 12. In this particular embodiment, a portion of the top edge 16 perimeter is sloped below the remainder of the top edge 16 perimeter. The sloped shape of the portion of the top edge 16 perimeter provides for ease of positioning the residual arm in the receptacle 12 and removing the residual arm from the receptacle 12 without compromising securement of the main socket 14 to a user's residual arm while the device 10 is in use. It will be apparent to one of ordinary skill in the art, however, that the shape and size of an exemplary top edge perimeter may be modified without necessarily departing from the scope of the present invention. Additionally, any number of different attachment devices such as hook and loop fastener straps, pinlock straps, buckles, some combination thereof, or the like may be employed to promote securement of a residual arm to an exemplary device without departing from the scope of the present invention.

Furthermore, in this particular embodiment, top edge links 18A-B are included to permit additional apparatuses or components to be connected to the main socket 14, such as by way of example not limitation, apparatuses that promote securement of the device 10 to the residual arm. As a specific example not by way of limitation, the top edge links 18A-B may define forearm links configured to establish connection between the main socket 14 and an upper socket adapted to surround at least a portion of the humerus, wherein each the main socket 14 and the upper socket may be rotated with respect to one another about the forearm links. Any number of different fasteners, clips, hinges, other mechanical joints, some combination thereof, or the like may be employed to establish rotatable connection between an exemplary main socket and upper socket without departing from the scope of the present invention.

The main socket 14 may be attached to the device stem 20 at a connection portion 22 of the main socket 14 by way of pins, fasteners, clips, joints, adhesive, welding, some combination thereof, or the like. In this particular embodiment, the main socket 14 may be rotated about a vertical axis (illustrated by line 15) to a number of different positions, and a user may introduce a pin to a pin hole 24 to axially secure the main socket 14 with respect to the stem 20. However, in certain alternative embodiments, the main socket may not necessarily be adapted to be rotated about the vertical axis (e.g., 15). Furthermore, in embodiments where the main socket is adapted to be axially rotated about the vertical axis (e.g., 15) to a number of different positions, it will be apparent to one of ordinary skill in the art that any number of different materials and/or mechanisms may be employed for axially securing the main socket 14 with respect to the stem 20 without departing from the scope of the present invention.

Figure 3:
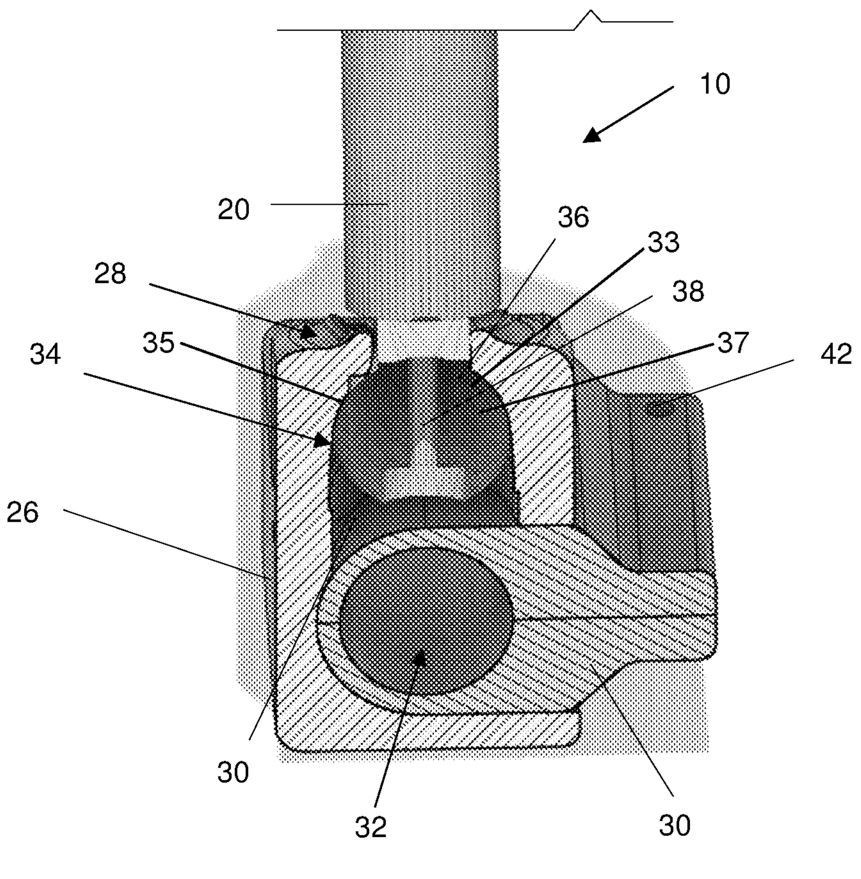
FIG. 3 is a perspective view of the handlebar containment unit of the FIG. 1 embodiment.

Referring to FIGS. 1-5, the stem 20 may extend from the connection portion 22 (e.g., below pin hole 24 in FIG. 4) of the main socket 14 to a joint portion 28 of a handlebar containment unit 26. Referring specifically to FIG. 3, an interior 34 of the joint portion 28 may comprise a ball and socket joint 36 mechanically connected 38 to the stem 20. Referring again to FIGS. 1-5, movement of the stem 20 may cause the ball and socket joint 36 to transmit force to a handlebar receiver 30 of the handlebar containment unit 26 to cause movement of a handlebar (e.g., handlebar 43 in FIG. 5). Mechanical communication between the main socket 14 and the handlebar (e.g., 43) may permit a user to use one's residual arm to steer or otherwise control the bicycle, and to balance one's position on the bicycle. In the embodiment shown, the ball and socket joint 36 is configured to permit rotation of the stem 20 in any direction with several degrees of freedom. It will be apparent to one of ordinary skill in the art that degrees of freedom of rotation of an exemplary stem may be varied according to any number of different desired ranges without departing from the scope of the present invention.

In certain exemplary embodiments, the main socket (e.g., 14), stem (e.g., 20) and handlebar containment unit (e.g., 26), including the joint portion 28 thereof, comprise 3D-printed, substantially plastic material. Exemplary 3D printing may involve resins, laser sintering, some combination thereof, or the like. It will be apparent to one of ordinary skill in the art, however, that any number of different materials and/or methods may be employed for assembling the aforementioned features without necessarily departing from the scope of the present invention.

Figure 4:
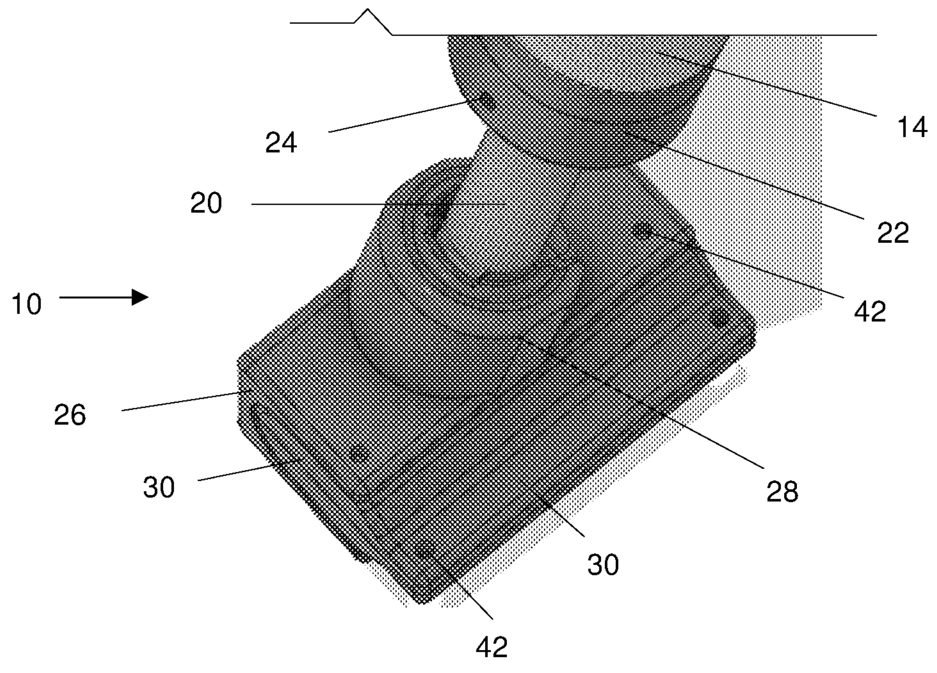
FIG. 4 is another perspective view of the handlebar containment unit of the FIG. 1 embodiment.

Referring again specifically to FIG. 3, the handlebar receiver 30 may define a perimeter of a handlebar channel 32, wherein the handlebar channel 32 may be specifically adapted to receive and secure a portion of a bicycle handlebar. In certain embodiments, the circumference of the handlebar channel 32 may be adjusted to receive and secure any number of different handlebars of various sizes and shapes. It will also be apparent to one of ordinary skill in the art that exemplary handlebar channels (e.g., 32) are not necessarily intended to be limited to use with bicycle handlebars, and exemplary embodiments of the present invention may be useful for promoting operation and control of any number of different handlebar vehicles. It will also be apparent to one of ordinary skill in the art that a handlebar adapter device removable from a handlebar is not necessarily required. By way of example and not limitation, an exemplary socket may be configured to rotate about an exemplary joint portion permanently integrated into an exemplary handlebar without necessarily departing from the scope of the present invention. Referring now to FIGS. 3 and 4, a plurality of fastener apertures 42 are shown. In this particular embodiment, securing bolts are used in the fastener apertures 42 to affix various segments and/or portions of the handlebar containment unit 26 to one another. It will be apparent to one of ordinary skill in the art, however, that there may be any number of different methods and/or materials available for combining various segments and/or portions of a handlebar containment unit, or for otherwise assembling a handlebar containment unit without necessarily departing from the scope of the present invention.

Referring specifically to FIG. 5, a handlebar 43 may be positioned and secured in a handlebar channel 32. Movement of the main socket 14 and stem 20 may cause movement of the handlebar containment unit 26, which in turn may cause movement of the handlebar 43. In certain exemplary embodiments, the stem (e.g., 20) further includes a length adjustment apparatus for providing user ability to adjust the overall length of the device based on, by way of example and not limitation, the height of the user, the size of the bike, the length and size of the residual arm, some combination thereof, or the like. As a specific example not by way of limitation, a connector piece may be positioned between and attached to the main socket (e.g., 14) and stem (e.g., 20), and configured to be adjusted between any number of different lengths to achieve a desired length (e.g., length of line 15) of the device 10 between the top edge 16 of the main socket 14 and the joint portion 28 of the handlebar containment unit 26. The connector piece may comprise machine metal. It will be apparent to one of ordinary skill in the art that there may be any number of different materials and/or methods available for providing length adjustment of an exemplary device without departing from the scope of the present invention.

Now referring to FIGS. 6-10, an alternative device 44 may comprise a main socket 14 defining a perimeter of a receptacle 12 adapted to receive a portion of a residual arm (not shown). In this particular embodiment, the main socket comprises 3D-printed plastic material. Using the residual arm, the user may apply pressure to the walls 55 or base 57 (see FIG. 7) of the receptacle 12 to direct force from the main socket 14 to a stem 20, which may act on a joint at a handlebar containment unit 52 to move the handlebar 60 secured thereto in accordance with the user's desired steering and controls. The top edge 16 of the main socket 14 may surround an entry and exit region for positioning the residual arm in the receptacle 12 and for removing the residual arm from the receptacle 12. In this particular embodiment, the top edge 16 is defined by a substantially continuous, smooth surface, which may promote user comfort.

Here, the main socket 14 may be attached to the device stem 20 at a connection portion 46 of the main socket 14 by way of pins, fasteners, clips, joints, adhesive, welding, some combination thereof, or the like. In this particular embodiment, the main socket is axially secured with respect to the stem 20. Different portions of the device 44 may be affixed to one another by fasteners 48, although fasteners are not necessarily required, and it will be apparent to one of ordinary skill in the art that there may be any number of different methods and/or materials available for affixing different portions or segments of the device 44 to one another without departing from the scope of the present invention.

Referring now to FIGS. 6 and 8-10, the stem 20 may extend from the connection portion 46 of the main socket 14 to a joint portion 54 of a handlebar containment unit 52. A mechanical connection 50 may extend from the stem 20 to a ball and socket joint 36, and rotation of the stem 20 may thus be translated to the ball and socket joint 36 through the mechanical connection 50. Range of motion of the ball and socket joint 36 may be partially restricted by an inner perimeter of the joint portion 54. It will be apparent to one of ordinary skill in the art that although a ball and socket joint is illustrated and described herein, any number of different mechanical joints, hinges or the like may be employed to provide rotational communication between an exemplary stem (e.g., 20) and handlebar containment unit (e.g., 52) without departing from the scope of the present invention. Movement of the stem 20 may cause the ball and socket joint 36 to transmit force to a handlebar receiver 58 of the handlebar containment unit 26 to permit steering of a bicycle 62 and to otherwise promote balance and control of the bicycle 62 (e.g., with respect to ground surface 64 in FIG. 9) and the user's position on the bicycle (e.g., with respect to seat 66 in FIG. 9).

Figure 9:
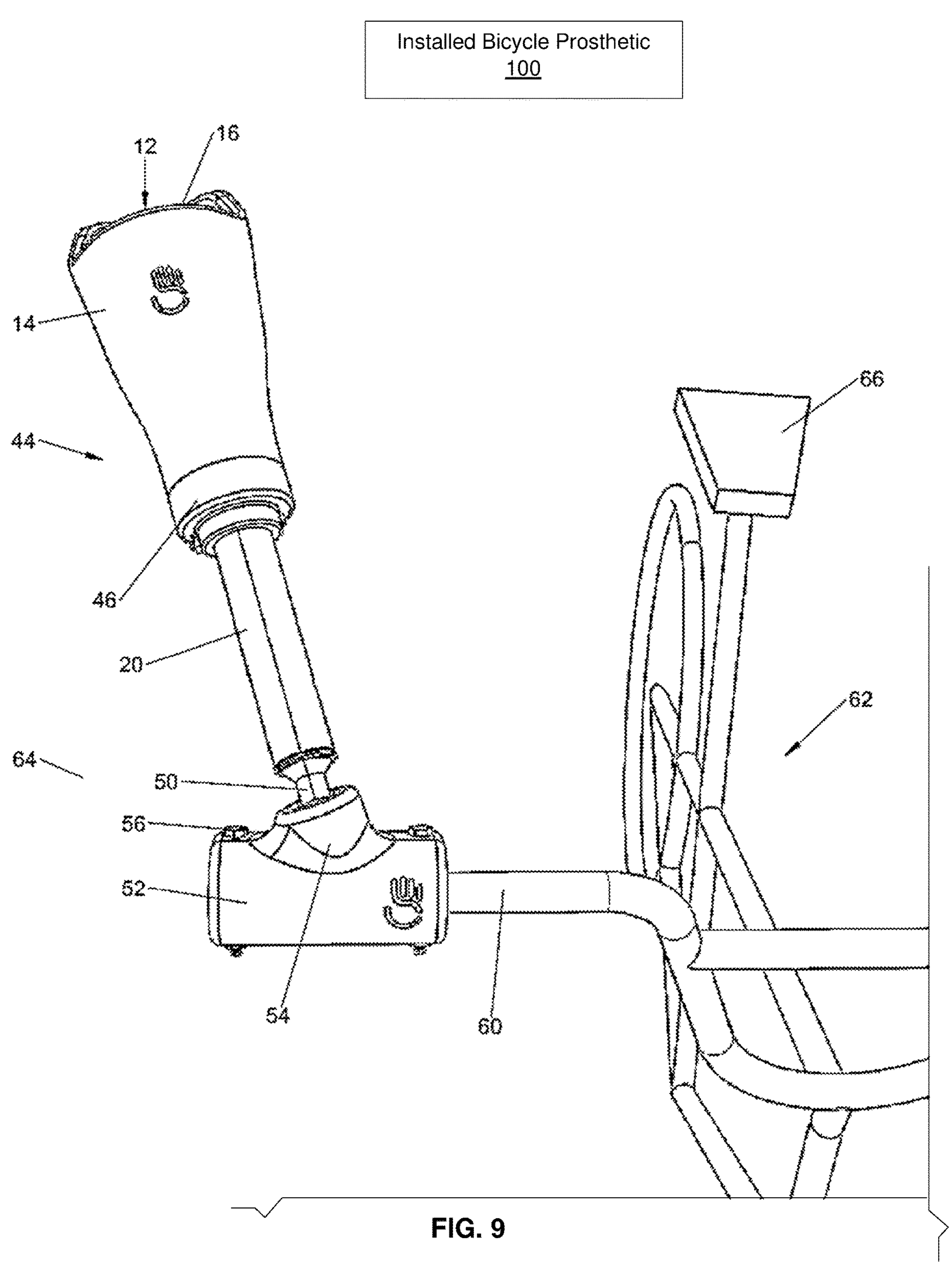
FIG. 9 is a perspective view of the device of the FIG. 6 embodiment installed on a bicycle.
Figure 10:
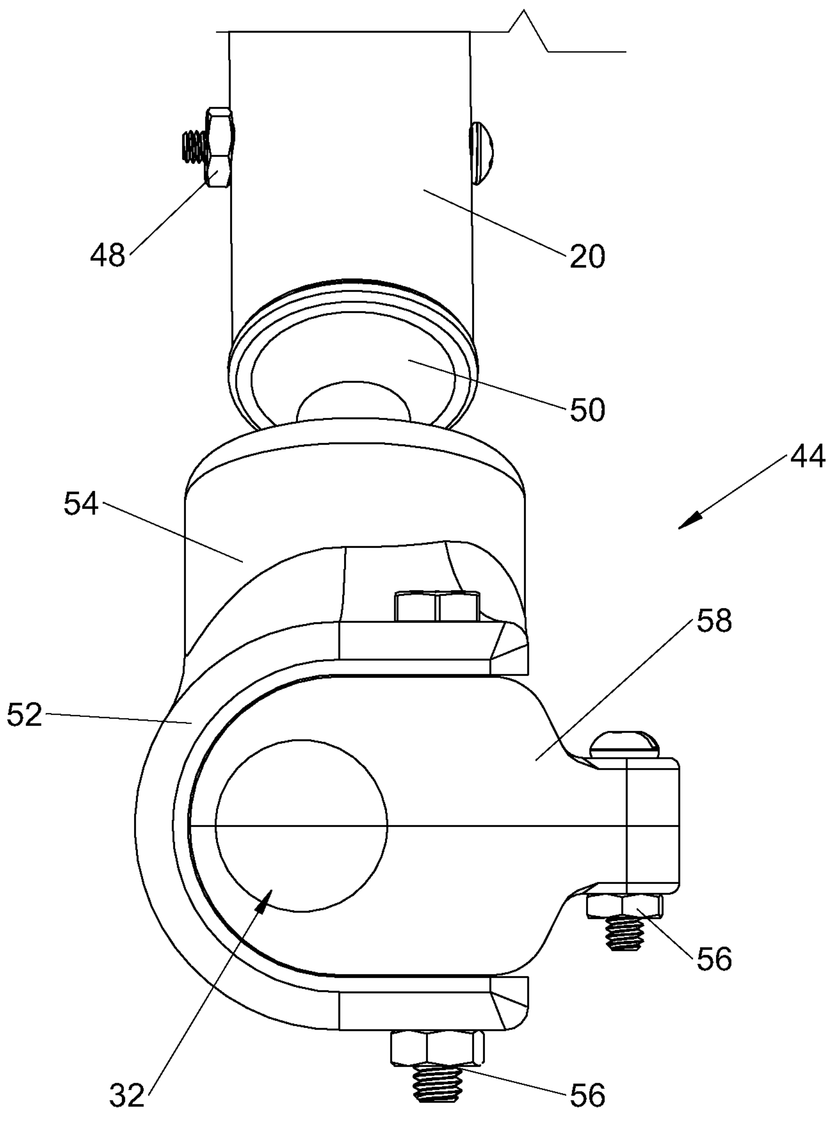
FIG. 10 is another perspective view of the handlebar containment unit of the FIG. 6 embodiment.
Figures 11, 12:
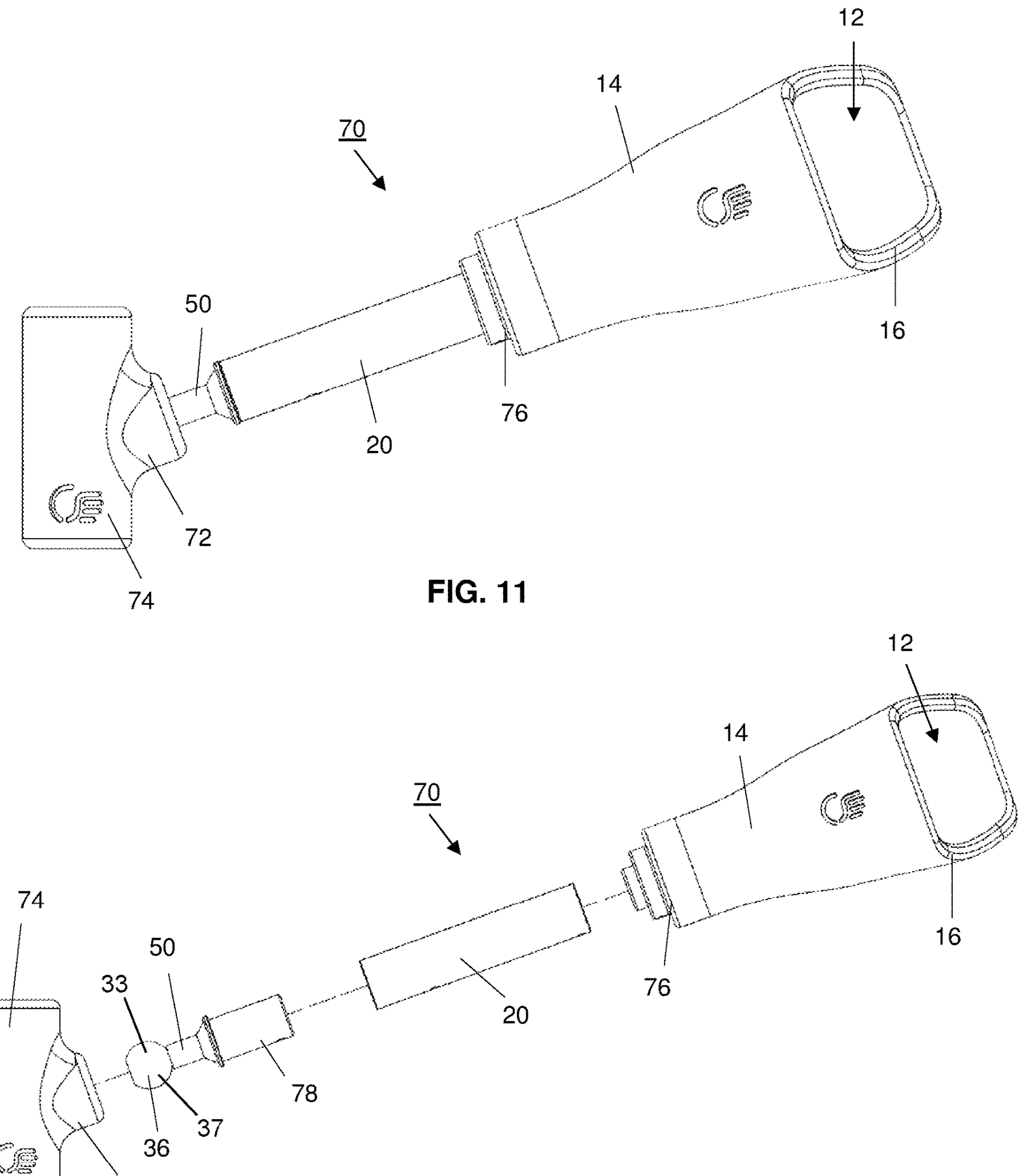
FIG. 11 is a top view of an alternative exemplary handlebar adapter device adapted to receive and secure a portion of a bicycle handlebar.
FIG. 12 is an exploded top view of the device of the FIG. 11 embodiment.
Figure 13:
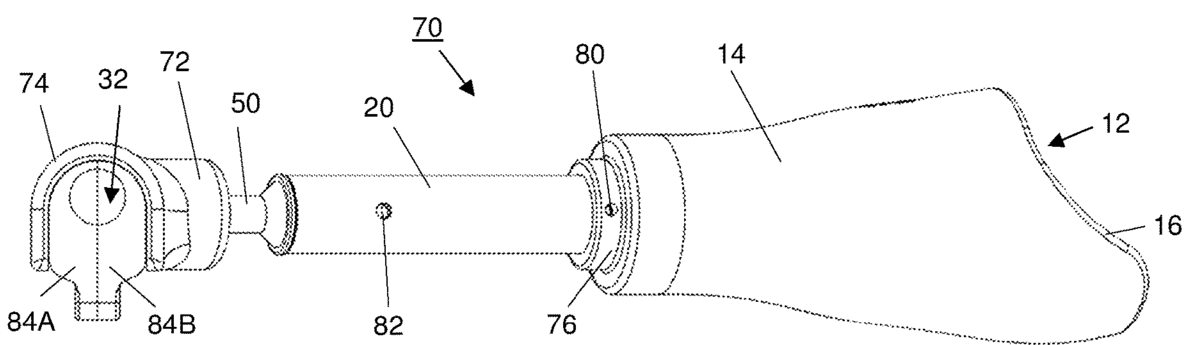
FIG. 13 is a right-side view of the device of the FIG. 11 embodiment, wherein a handlebar containment unit is positioned to receive and secure a portion of a bicycle handlebar.
Figure 14:
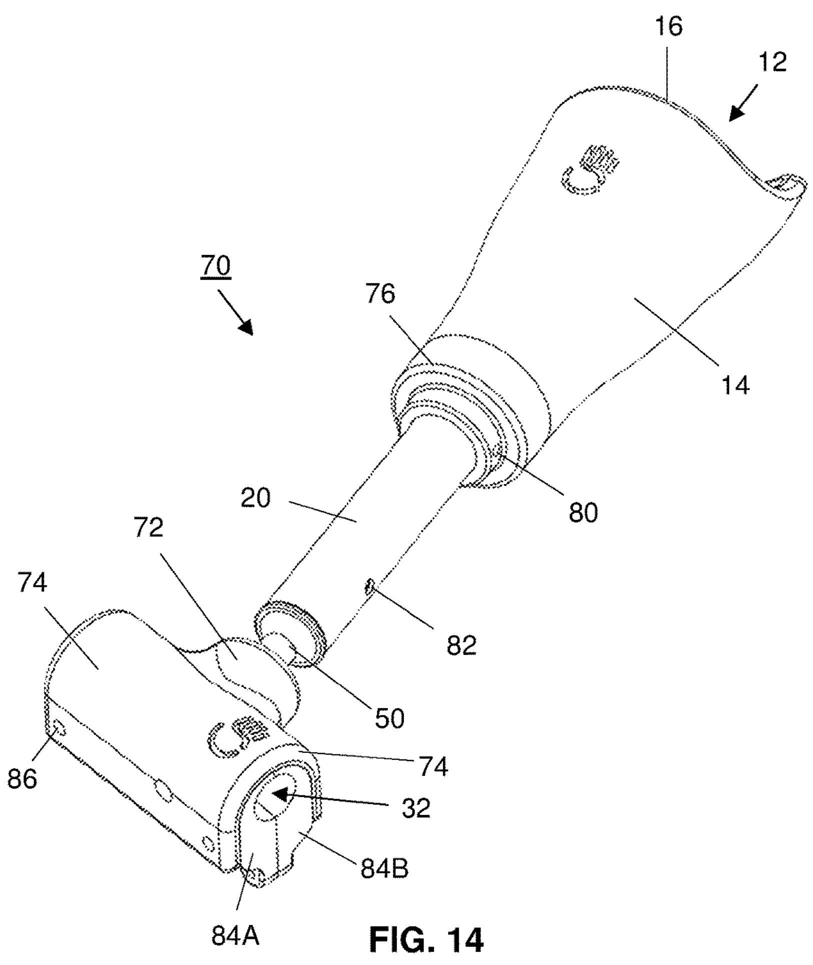
FIG. 14 is a perspective view of the device of the FIG. 11 embodiment.
Figure 15:
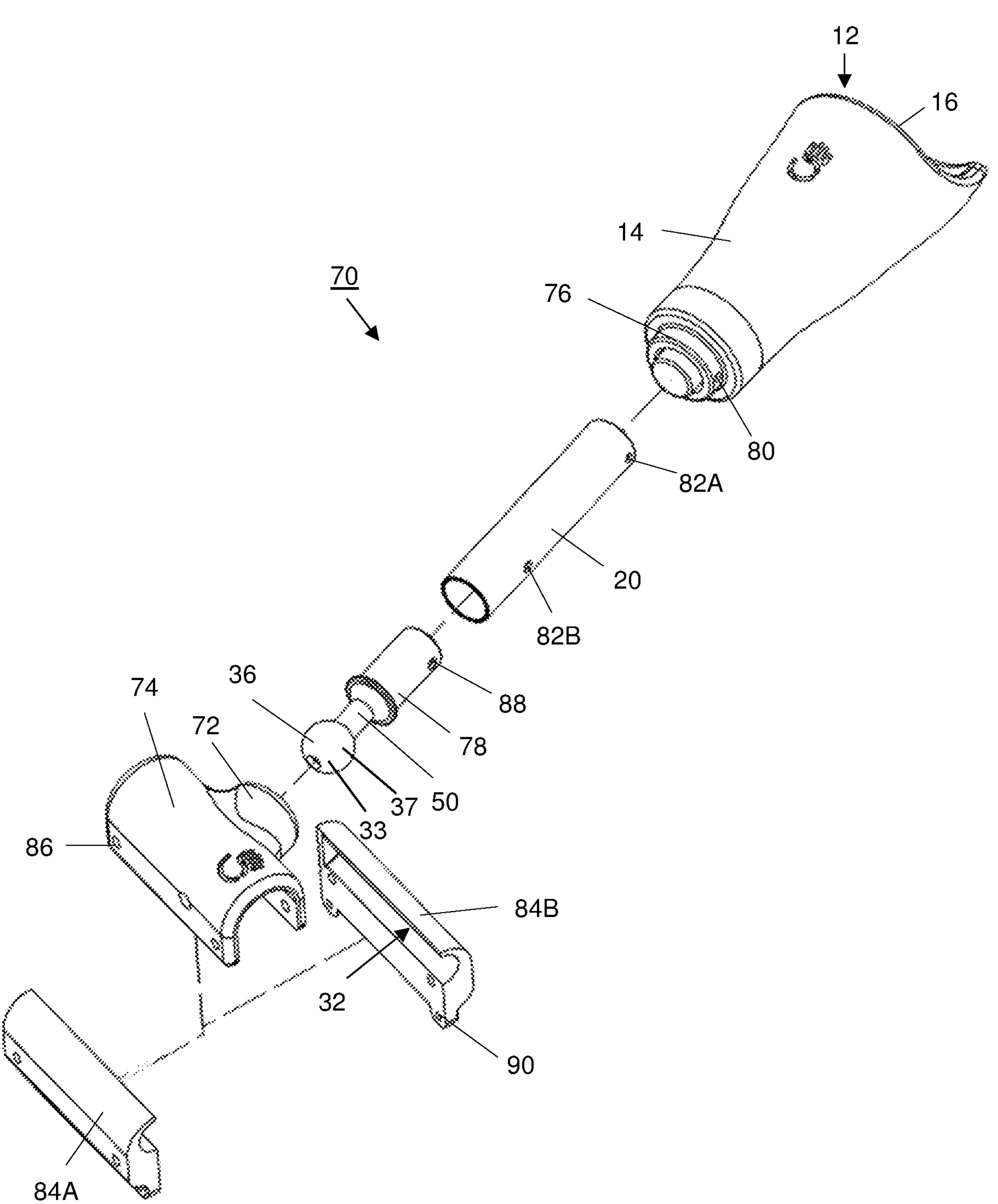
FIG. 15 is an exploded perspective view of the device of the FIG. 11 embodiment.
Figure 16:
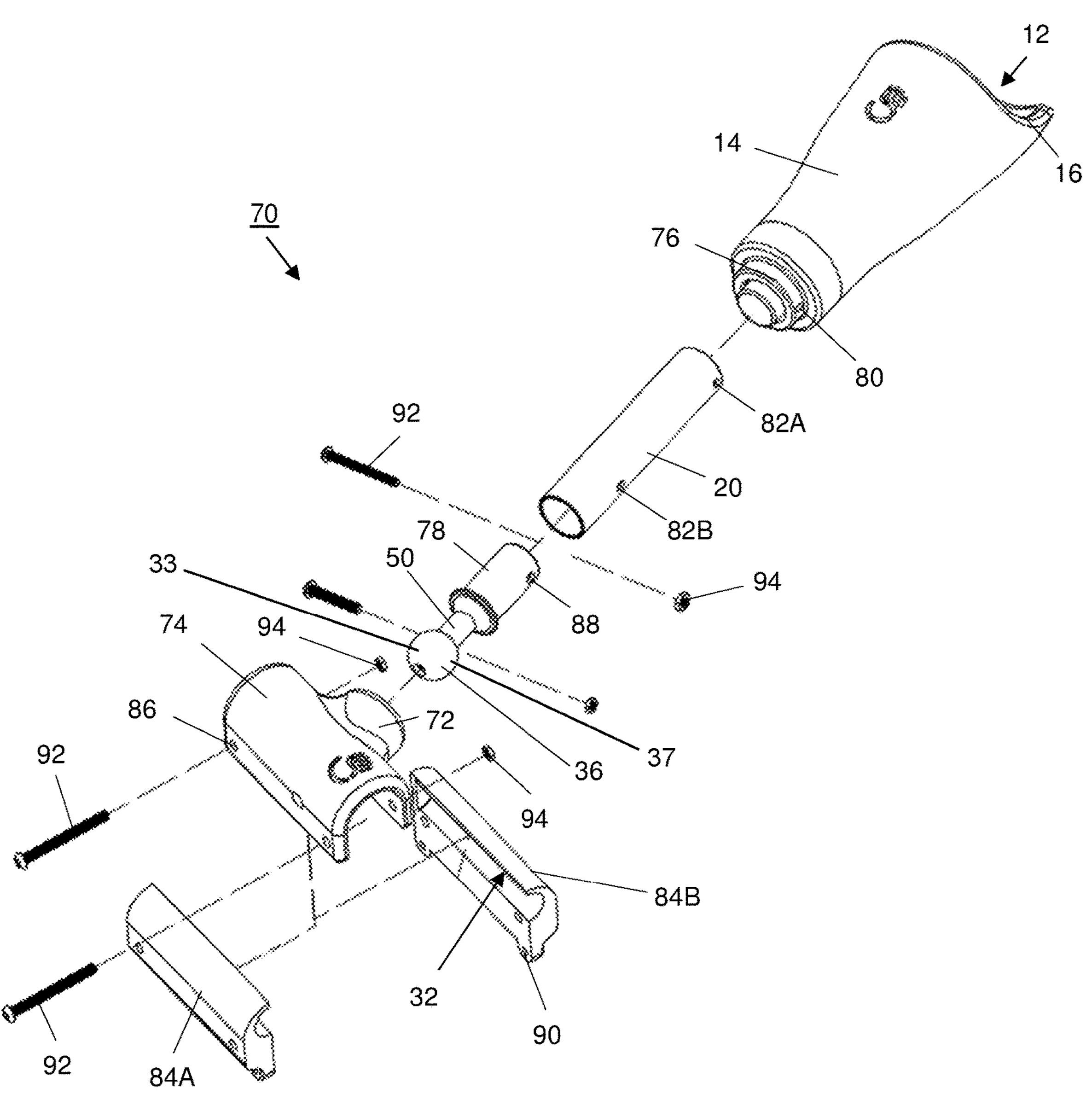
FIG. 16 is another exploded perspective view of the device of the FIG. 11 embodiment.
Figure 17:
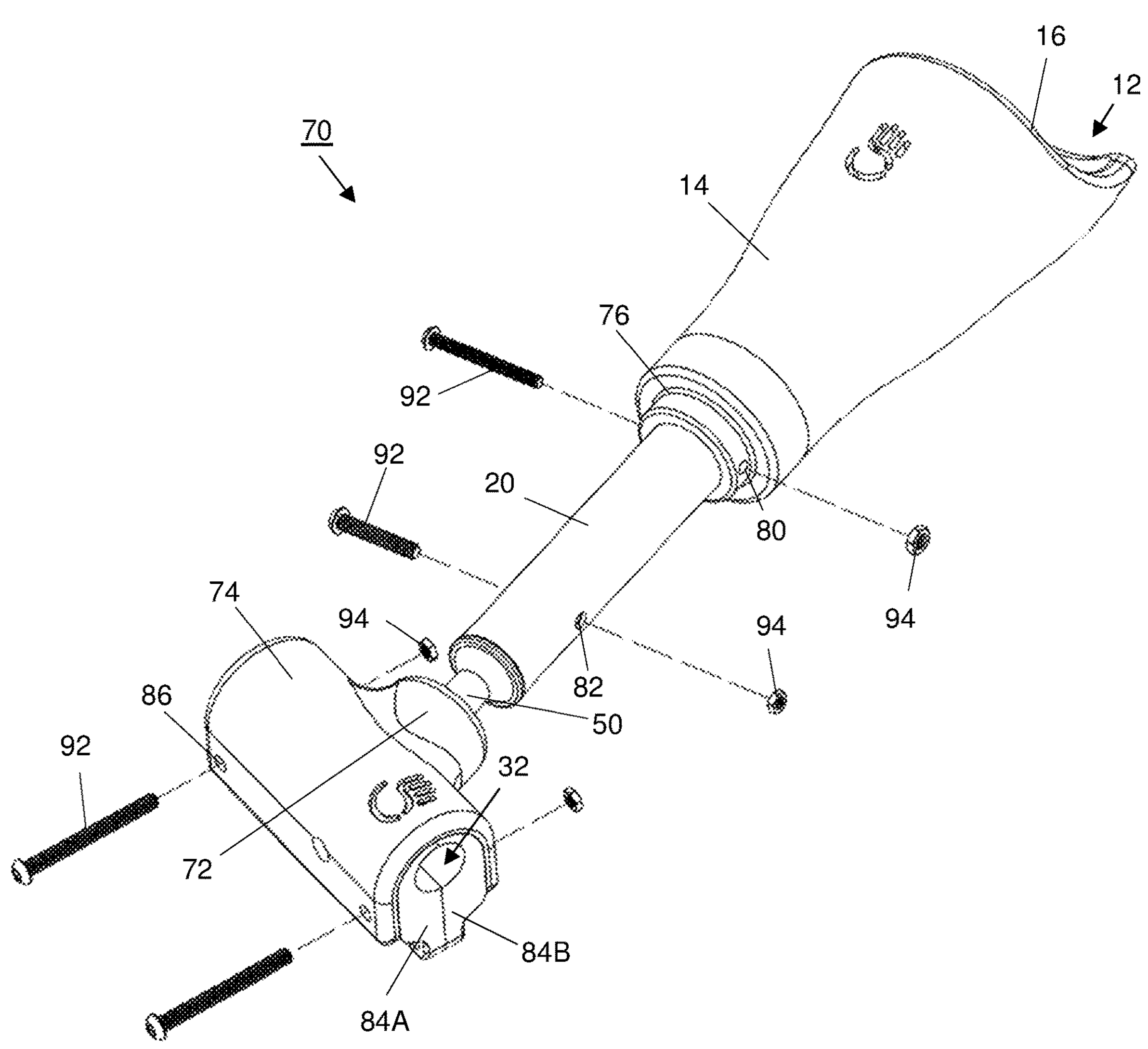
FIG. 17 is yet another exploded perspective view of the device of the FIG. 11 embodiment.
Figure 18:
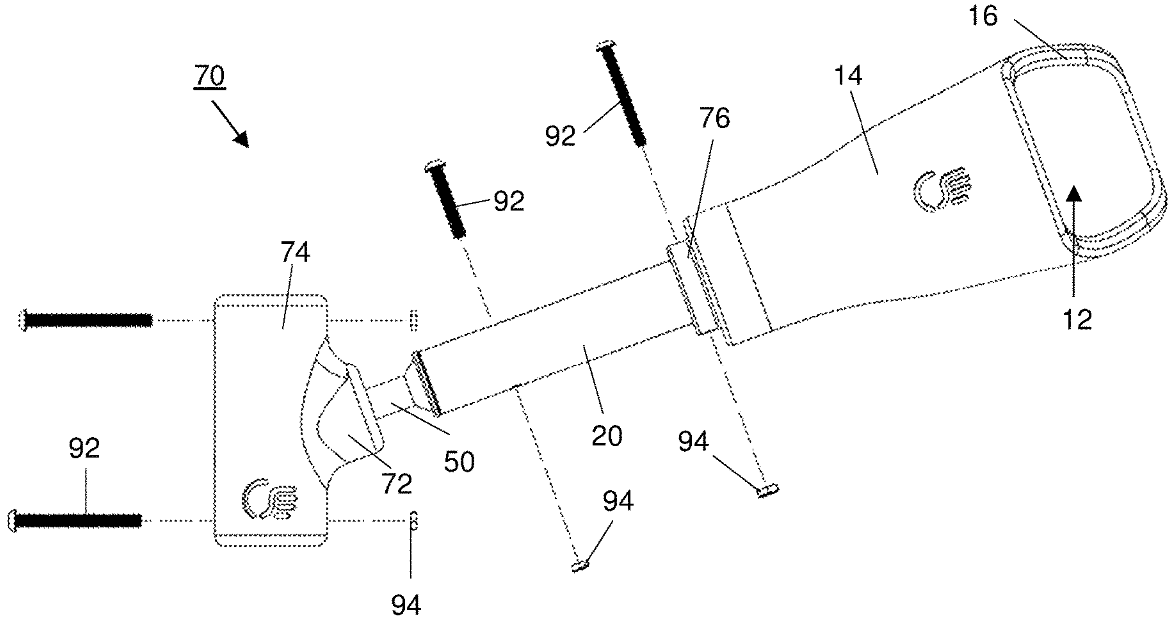
FIG. 18 is another exploded top view of the device of the FIG. 11 embodiment.
Figure 19:
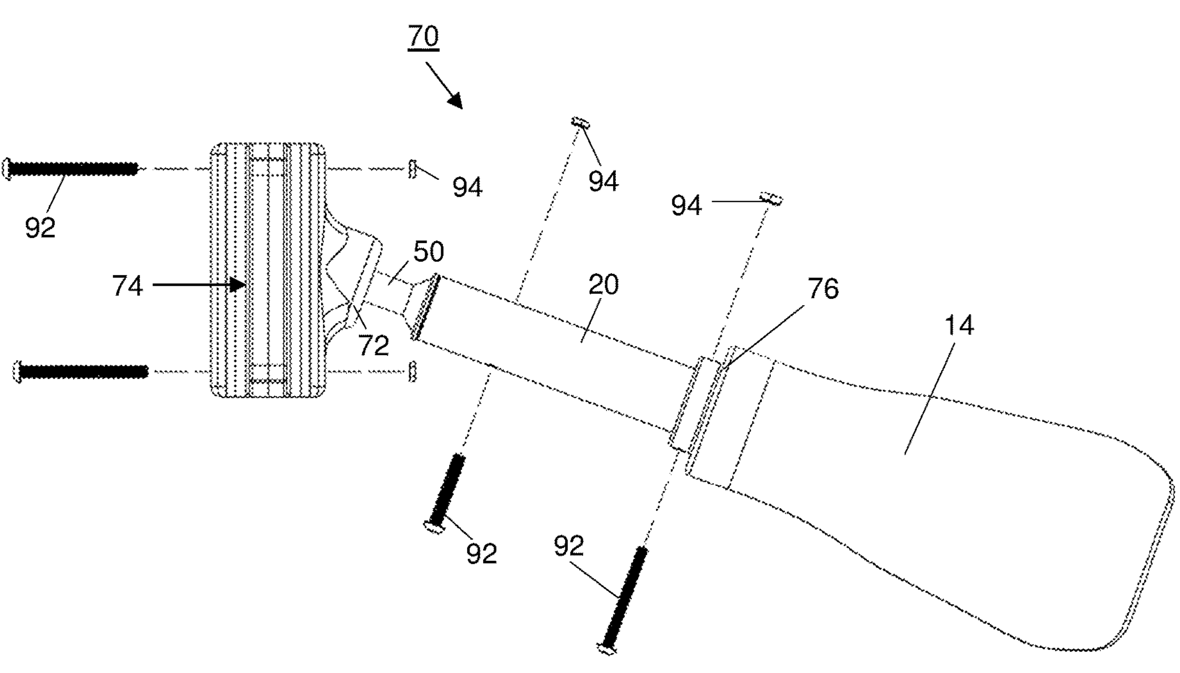
FIG. 19 is an exploded bottom view of the device of the FIG. 11 embodiment.
Figure 20:
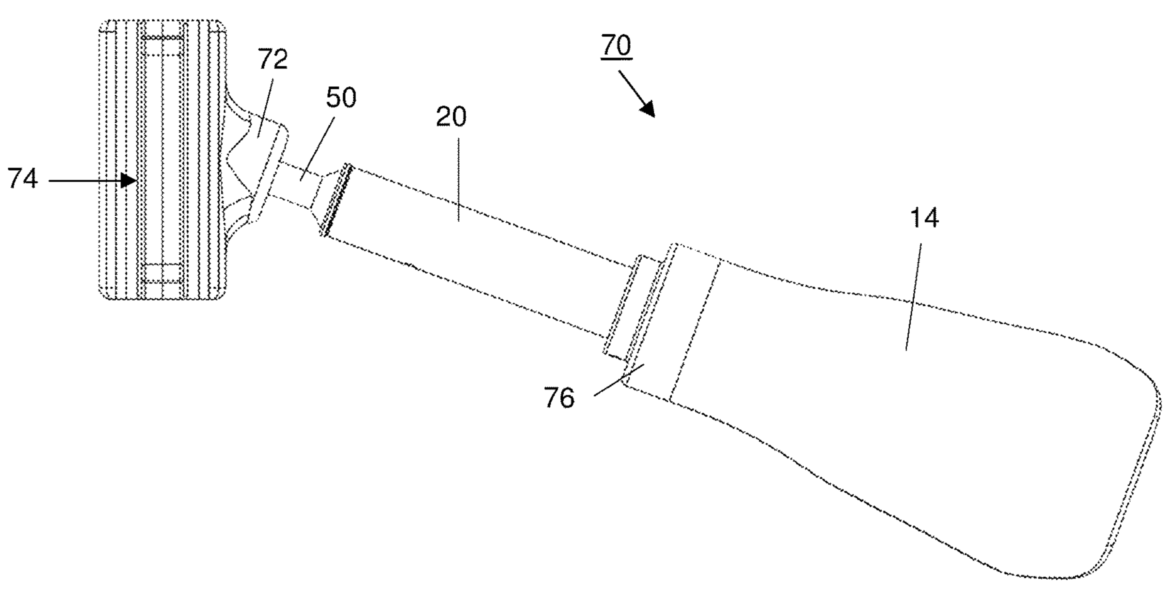
FIG. 20 is a bottom view of the device of the FIG. 11 embodiment.
Figure 21:
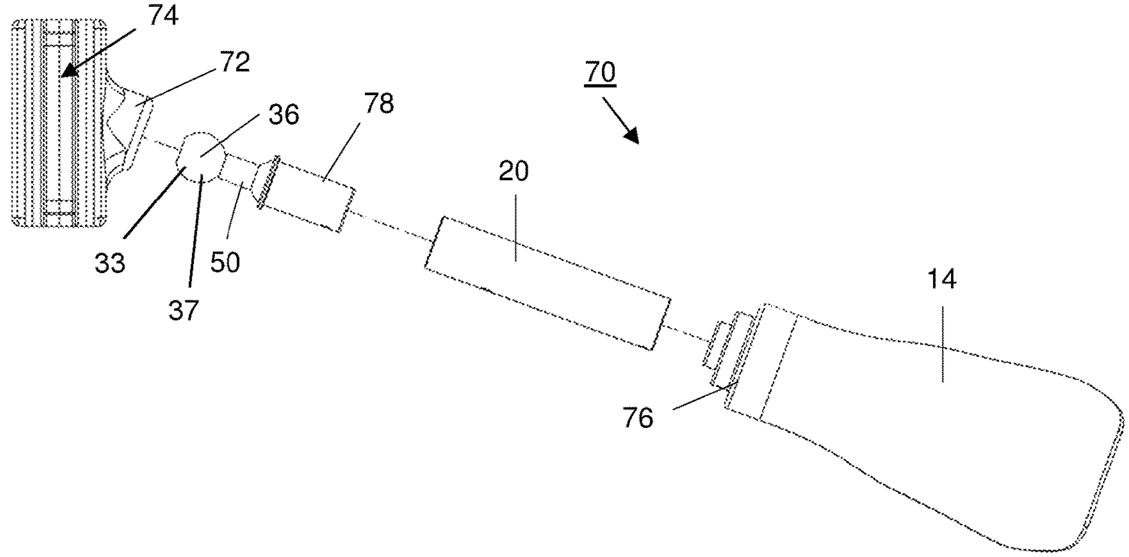
FIG. 21 is another exploded bottom view of the device of the FIG. 11 embodiment.
Figure 22:
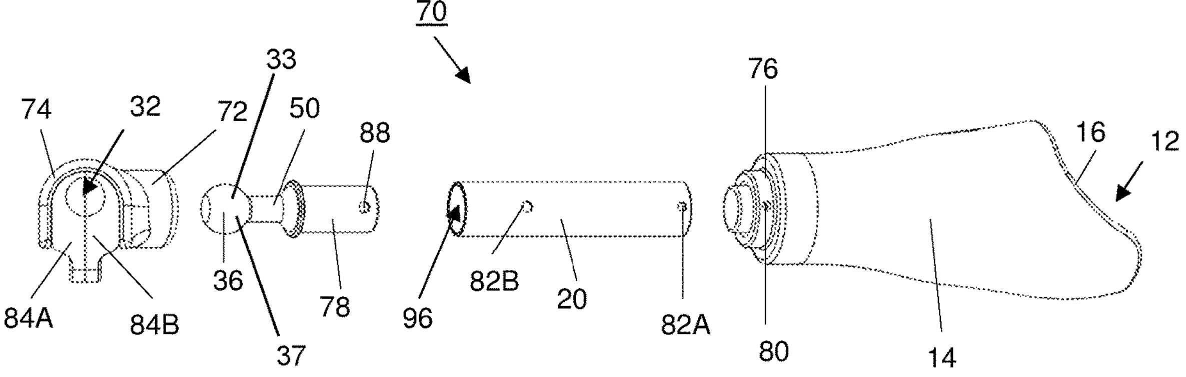
FIG. 22 is an exploded right-side view of the device of the FIG. 11 embodiment, wherein a handlebar containment unit is positioned to receive and secure a portion of a bicycle handlebar.

Referring specifically to FIG. 10, the handlebar receiver 58 may define a perimeter of a handlebar channel 32, wherein the handlebar channel 32 is specifically adapted to receive and secure a portion of a bicycle handlebar. A plurality of fasteners 56 are shown in FIGS. 6, 8-10 affixing varying segments or parts of the device 44 to one another. In alternative embodiments, fasteners may not necessarily be required. Referring specifically to FIG. 9, the device 44 is installed 100 on a right-side handlebar of a bicycle 62. It will be apparent to one of ordinary skill in the art, however, that exemplary embodiments of the present invention may be installed on or secured to either side or even both sides of a handlebar apparatus of a handlebar vehicle without departing from the scope of the present invention.

Referring now to FIGS. 11-22, an alternative device 70 comprising a main socket 14 (including a top edge 16 surrounding an entry and exit region for positioning a residual arm in a receptacle 12), a stem 20, a connection portion 76 of the main socket 14 (configured to attach the stem 20 to the main socket 14), a mechanical connection 50 extending from the stem 20 to a ball and socket joint 36, and a handlebar containment unit 74, including a handlebar channel 32 thereof is shown. The handlebar containment unit 74 may include a joint portion 72 configured to provide several degrees of freedom of rotation of the stem 20. It will be apparent to one of ordinary skill in the art that certain exemplary joint portions may be adjustable to provide variable degrees of freedom of rotation of the stem.

A stem connector 78 may be configured to connect the mechanical connection 50 and ball and socket joint 36 to the stem 20. In the embodiment shown, a bolt 92 is positioned in apertures 82B, 88 of each the stem 20 and stem connector 78, and the bolt 92 is secured by a nut 94, affixing the stem 20 to the stem connector 78. The mechanical connection 50 may be affixed to the stem connector 78 and the ball and socket joint 36 by way of welding, fasteners, clips, adhesive, some combination thereof, or the like. In this particular embodiment, the stem connector 78 and the stem 20 are each hollow (e.g., 96). The aforementioned hollow configuration may be advantageous for reducing the weight of the device 70. However, it will be apparent to one of ordinary skill in the art that hollow configurations of the stem and stem connector are not necessarily required, and there may be any number of different methods and/or materials available for assembling an exemplary stem without departing from the scope of the present invention. It will also be apparent to one of ordinary skill in the art that a stem connector is not necessarily required to permit attachment between the stem and the rotation feature at the joint portion (e.g., mechanical connection 50 and ball and socket joint 36). The stem may be rotatably attached to the joint portion by way of any number of different methods and/or materials without departing from the scope of the present invention.

In the embodiment shown, a bolt 92 is positioned in apertures 80, 82A of each the connection portion 76 of the main socket 14 and the stem 20, and the bolt 92 is secured by a nut 94, affixing the stem 20 to the main socket 14. It will be apparent to one of ordinary skill in the art, however, that the main socket may be attached to the stem by way of any number of different methods and/or materials without departing from the scope of the present invention. In this particular embodiment, the handlebar channel 32 may be defined by each of two connected, opposing, substantially symmetrical portions 84A, 84B of a handlebar receiver 84. The handlebar receiver portions 84A, 84B may be affixed to one another by positioning a bolt 92 in apertures 86, 90 of each handlebar receiver portion 84A, 84B and an outer portion of the handlebar containment unit 74, and securing the bolt 92 with a nut 94. It will be apparent to one of ordinary skill in the art, however, that there may be any number of different methods and/or materials available for assembling an exemplary handlebar containment unit without departing from the scope of the present invention.

Referring to FIGS. 3, 8, 12, 15, 16, 21, and 22, the ball 37 of the ball and socket joint 36 represents an interface 33 between the interior 34 of the joint portion 28 as the socket 35 and the stem 20 extending from the ball 37.

Any embodiment of the present invention may include any of the features of the other embodiments of the present invention. The exemplary embodiments herein disclosed are not intended to be exhaustive or to unnecessarily limit the scope of the invention. Exemplary embodiments related to bicycles were chosen and described in order to explain the principles of the present invention so that others skilled in the art may practice the invention. Having shown and described exemplary embodiments of the present invention, those skilled in the art will realize that many variations and modifications may be made to the described invention, and that the present invention is not intended to be limited to use with bicycles. The present invention may be useful for promoting operation and control of any number of different handlebar vehicles. Many variations and modifications will provide the same result and fall within the spirit of the claimed invention. It is the intention, therefore, to limit the invention only as indicated by the scope of the claims.

What is claimed is:

1. A limb differential handle adapter, comprising:

a split coupling mount configured to removably attach to a handle, the split coupling mount including a lower portion having a lower curved channel disposed in an upper surface of the lower portion and an upper portion having an upper curved channel disposed in a lower surface of the upper portion such that as reversibly assembled the lower curved channel and the upper curved channel cooperate to form a coupling conduit having an internal surface configured to contact the handle around a periphery of the handle, the split coupling mount further including a plurality of fasteners spaced along an elongate dimension of the handle configured to reversibly tighten the upper portion to the lower portion;

a rotational joint configured to removably attach to and extend from an upper surface of the upper portion of the split coupling mount at an angle relative to the coupling conduit, the rotational joint including a socket, an interface disposed in the socket, and a shaft extending from the interface; and a differential limb socket configured to receive a differential limb, the differential limb socket being removably coupled to the rotation joint.

2. The limb differential handle adapter of claim 1, wherein the limb differential handle adapter is free of locking mechanisms restricting disengagement of the differential limb from the differential limb socket.

3. The limb differential handle adapter of claim 1, wherein the rotational joint is a ball-and-socket joint.

4. The limb differential handle adapter of claim 1, wherein the differential limb socket is attached to the shaft of the rotational joint.

5. The limb differential handle adapter of claim 1, wherein the differential limb socket is attached to the socket of the rotational joint.

6. The limb differential handle adapter of claim 1, wherein the handle is a handlebar.

7. The limb differential handle adapter of claim 6, wherein the handlebar is a bicycle handlebar.

8. The limb differential handle adapter of claim 6, wherein the handlebar is a motorcycle handlebar, a moped handlebar, an all-terrain vehicle handlebar, a jet ski handlebar, or a snowmobile handlebar.

9. The limb differential handle adapter of claim 1, wherein the handle is a stroller, carriage, cart, or hand truck handle.

* * * * *